(12) United States Patent
Luo

(10) Patent No.: US 7,923,401 B2
(45) Date of Patent: Apr. 12, 2011

(54) SINGLE-SITE CATALYST ACTIVATORS, PROCESSES FOR MAKING SAME, AND USE THEREOF IN CATALYSTS AND POLYMERIZATION OF OLEFINS

(75) Inventor: Lubin Luo, Baton Rouge, LA (US)

(73) Assignee: Albermarle Corporation, Baton Rouge, LA (US)

( * ) Notice: Subject to any disclaimer, the term of this patent is extended or adjusted under 35 U.S.C. 154(b) by 0 days.

(21) Appl. No.: 12/303,045

(22) PCT Filed: May 10, 2007

(86) PCT No.: PCT/US2007/068664
§ 371 (c)(1),
(2), (4) Date: Dec. 1, 2008

(87) PCT Pub. No.: WO2007/143328
PCT Pub. Date: Dec. 13, 2007

(65) Prior Publication Data
US 2009/0247398 A1 Oct. 1, 2009

Related U.S. Application Data

(60) Provisional application No. 60/809,231, filed on May 30, 2006.

(51) Int. Cl.
*B01J 31/12* (2006.01)
(52) U.S. Cl. .................................................. 502/171
(58) Field of Classification Search .................. None
See application file for complete search history.

(56) References Cited

U.S. PATENT DOCUMENTS 6,232,261 B1 * 5/2001 Little ............................ 502/158
6,414,099 B1 * 7/2002 Hlatky et al. ................. 526/161

FOREIGN PATENT DOCUMENTS

WO WO 2006/004789 A2 1/2006

OTHER PUBLICATIONS

WIPO written opinion of the international searching authority.*
Akihiro Yano, et al; "Influence of Activators on Ethylene Polymerization With Diphenylmethylidene-(cyclopentadienyl)(fluorenyl)zirconium Dichloride Catalysts At High Temperature"; Journal of Molecular Catalysis A:Chemical; 1999; p. 77-86; vol. 148; Elsevier Science B.V.; Amsterdam, Netherlands.
Wigand Braune, et al; "Aluminum Complexes With Sulfide-Linked Bis(phenolato) Ligands: Unusual Structure and Reactivity of the Methyl Bis(phenolato) Complex "[Al(tbmp)Me]" (tbmp=2,2'-ThiobisI(6-tert-butyI-4-methylphenolato))"; Organometallics; 2005; p. 1953-1958; vol. 24; American Chemical Society; Washington, D.C., US.
Zofia Janas, et al; "Homo- and Heterometallic Alumimum and Titanium Complexes of Tridentate (OSO) Ligand: Synthesis, Structure, and Catalytic Activity"; Organometallics; 2005; p. 3987-3994; vol. 24; American Chemical Society; Washington, D.C., US.
Stefan Fokken; "Nine-Membered Titanacyclic Complexes Based on an Ethylene-Bridged Bis(phenolato) Ligand: Synthesis, Structure, and Olefin Polymerization Activity"; Organometallics; 1997; p. 4240-4242; vol. 16; American Chemical Society; Washington, D.C., US.
Holleck, L., et al; "Polarographic Reduction of Solochrome Violet RS and the Mechanism of Complexing With Aluminum in Methanol Solution"; Journal of Electroanalytical Chemistry and Interfacial Electrochemistry; 1969; p. 287-296; vol. 20; Elsevier Sequoia S.A.; Lausanne, The Netherlands.

* cited by examiner

*Primary Examiner* — Melvin C Mayes
*Assistant Examiner* — Stefanie Cohen
(74) *Attorney, Agent, or Firm* — James A. Jubinsky

(57) ABSTRACT

Single-site catalyst activator compositions are provided, said activator compositions comprising anion/cation ion pair wherein; (a) the anion comprises a metal atom bonded via hetero atoms to a chelating organic ligand, and (b) the cation comprises a Bronsted acid.

15 Claims, No Drawings

SINGLE-SITE CATALYST ACTIVATORS, PROCESSES FOR MAKING SAME, AND USE THEREOF IN CATALYSTS AND POLYMERIZATION OF OLEFINS

FIELD OF THE INVENTION

The present invention relates to single-site catalyst activators, processes for making same, and their use in polymerization of olefin compounds.

BACKGROUND

Ziegler-Natta type catalysts for the polymerization of olefins are well known. The traditional Ziegler-Natta type soluble systems comprise a metal halide activated to a catalyst species by reaction with a metal alkyl cocatalyst, particularly an aluminum alkyl cocatalyst. The activation of these traditional heterogeneous Ziegler-Natta catalysts generates a variety of different active sites. As a consequence of this non-uniformity of active sites, the catalysts produce polymer products having a broad molecular weight distribution (MWD). Furthermore, the polymer products exhibit broad composition distribution (CD), poor comonomer incorporation and block sequence distribution.

Catalysts formed when a bis(cyclopentadienyl) compound of the Group 4 metals, including zirconium and hafnium, is activated by an alumoxane, i.e., metallocene-alumoxane catalysts, whether homogeneous or supported, generally possess higher activity and are more versatile than conventional Ziegler-Natta type catalysts. These catalysts are part of a broader category of single-site catalysts, which have been used to produce a variety of polymer products including, for example, high density linear polyethylene (HDPE), linear low density polyethylene (LLDPE), ethylene-propylene copolymer (EP), non-crystalline polypropylene and crystalline polypropylene. Metallocene-alumoxane and other single-site catalysts offer the advantage over traditional Ziegler-Natta catalysts of being able to produce polymers with narrower MWD. Nonetheless, metallocene-alumoxane catalysts have limitations in practical commercial applications. Aluminoxane activators are relatively expensive because usually a substantial excess of aluminoxane to metallocene is required. Aluminoxane is also air sensitive/water reactive and is challenging to handle due to tendency to gel. Furthermore, metallocene-aluminoxane catalyst, while producing a relatively narrow MWD polymer product, has limited capability to produce high molecular weight polymers or polymers having a high comonomer content.

European patent applications 88300698.3 and 88300699.1, published in 1988 under publication numbers 277,003 and 277,004, respectively, describe ionic single-site catalysts with non-aluminoxane activators for activating bis (cyclopentadienyl)-substituted Group 4 metal based metallocenes. The activator is described in 277,003 as comprising a cation capable of donating a proton and reacting irreversibly with a ligand of the metallocene to liberate a free, neutral by-product and a compatible noncoordinating anion comprising a plurality of boron atoms, which compatible noncoordinating anion is stable, bulky and labile. The activator is described in 277,004 as an ion-exchange compound comprising a cation that will irreversibly react with at least one ligand of the metallocene and an anion that is a single coordination complex comprising a plurality of lipophilic radicals covalently coordinated to and shielding a central formally charge-bearing metal or metalloid atom, which anion is bulky, labile and stable to any reaction involving the cation of the second component. U.S. Pat. No. 5,153,157 describes similar catalyst systems with an additive that removes impurities and gives examples of such systems based on perfluoro groups.

An article published in Organometallics 2000, 19, 1625-1627, "Al-, Nb-, and Ta-Based Perfluoroaryloxide Anions as Cocatalysts for Metallocene-Mediated Ziegler-Natta Olefin Polymerization" by Yimin Sun, Matthew V. Metz, Charlotte L. Stern, and Tobin J. Marks, reports on ionic activator compound based on the pentafluorophenoxide group $C_6F_5O^-$. This article also illustrates how single-site catalysts based on such activator compounds deactivate rather easily because pentafluorophenoxide group tends to be easily withdrawn from the activator due to interaction with the metallocene.

The systems based on perfluoro groups appear to rely on these groups as electron-withdrawing groups for stabilization. This has a stabilizing effect. As used herein, the term "electron-withdrawing" means capable of reducing electron density on a reaction center and the term "electron-donating" means capable of increasing electron density on a reaction center. Catalysts based on perfluoro groups tend to be relatively expensive. Another technique used for stabilization is chelating ligands. US Publication Number 2006/0009596 describes a borate with chelating ligands used for activating a single-site catalyst; yet the catalyst systems described must be fluorinated, preferably perfluorinated.

In spite of published descriptions of ionic single-site catalyst systems, it is observed that most of these systems are still based on relatively expensive perfluoro groups. A need exists for commercially feasible ionic, single-site catalyst activators that permit suitable control of molecular weight and molecular weight distribution in polymers and at the same time remain intact, without significant deactivation, for commercially acceptable periods of time.

SUMMARY OF THE INVENTION

This invention provides activator compositions that fulfill the current need and are capable of activating metallocene and non-metallocene single-site catalyst precursors. Activator compositions according to this invention are ion pairs in which the cation comprises a Bronsted acid. An organic ligand of the anion has at least two hetero atoms chelated to a metal atom through covalent bonding.

It is believed that the fact that the organic ligand is chelated with the metal atom, adds stability to the activator composition and significantly decreases the tendency to deactivate, especially as to ligands bearing no electron-withdrawing group. A benefit of this invention is that typically expensive components having ligands with one or more electron-withdrawing groups are not required for stabilization of the activator composition. Activator compositions of this invention may contain one or more ligands with one or more electron-withdrawing groups, but an electron-withdrawing group bearing ligand is not required. As used herein, the term "hetero atom" means atoms other than carbon and hydrogen including atoms from Groups 15, 16, and 17, such as O, S, N, and P (as identified in a Periodic Table of the Elements using new IUPAC format (i.e., current IUPAC format)); and the term "Bronsted acidic" means: capable of donating a proton.

In somewhat greater detail, this invention provides activator compositions comprising an anion/cation ion pair, wherein (a) the anion comprises (i) a metal atom and (ii) an organic ligand having at least two hetero atoms and being chelated to the metal atom through covalent bonding of at least the two hetero atoms with the metal atom, and (b) the cation comprises a Bronsted acid. Also provided are such activator compositions wherein the metal atom comprises a metal selected from Groups 2-10, Group 13, or the lanthanide or actinide series of the Periodic Table of the Elements, e.g., wherein the metal atom comprises Al. Also provided are such activator compositions wherein the Bronsted acid comprises $[HA_K]^+$, wherein H is a proton, A comprises a neutral Lewis base, x is 0, 1 or 2, and when x is 2, the A's are the same or different. Also provided are such activator compositions derived from at least: (a) $M'^{m+}Q_m$, where M' is a metal selected from Groups 2-10, Group 13, Lanthanide group, or Actinide group; m is the valence of the metal M'; and each Q independently comprises at least one or more of: halide radical, dialkylamido radical, alkoxide radical, aryloxide radical, hydrocarbyl radical, substituted-hydrocarbyl radical, and organometalloid radicals; and (b) $H_y$(Ch-L), wherein (i) y is 2, 3, or 4; (ii) Ch-L is an organic ligand comprising y hetero atoms, at least two of the y hetero atoms being capable of forming a covalent bond with the metal M', and (iii) $H_y$ is y hydrogen radicals, each hydrogen radical being bonded to one of the y hetero atoms; additionally such activator compositions derived from: (c) neutral Lewis base and, optionally, (d) support. Also provided are activator compositions derived from at least: (a) $M'^{m+}Q_m$, where M' is a metal selected from Groups 2-10, Group 13, Lanthanide group, or Actinide group; m is the valence of the metal M'; and each Q independently comprises at least one or more of: halide radical, dialkylamido radical, alkoxide radical, aryloxide radical, hydrocarbyl radical, substituted-hydrocarbyl radical, and organometalloid radicals; and (b) $H_y$(Ch-L), wherein (i) y is 2, 3, or 4; (ii) Ch-L is an organic ligand comprising (y+q) hetero atoms, at least two of the y hetero atoms being capable of forming a covalent bond with the metal M', q is 0, 1 or 2, and, optionally, one or more of the q hetero atoms is capable of forming a coordinate covalent bond with the metal M', and (iii) $H_y$ is y hydrogen radicals, each hydrogen radical being bonded to one of the y hetero atoms. Also provided are activator composition comprising a metal atom, an organic ligand, and a Bronsted acid, wherein: (a) the organic ligand comprises at least y hetero atoms and is chelated to the metal atom through covalent bonding of at least two of the y hetero atoms with the metal atom; and (b) the Bronsted acid comprises $[HA_x]^+$, wherein H is a proton, A comprises a neutral Lewis base, and x is 0, 1 or 2, and when x is 2, the A's are the same or different; for example, wherein the neutral Lewis base comprises: a) one or more linear ethers, one or more cyclic ethers or mixtures thereof or b) one or more secondary amines, one or more tertiary amines, or mixtures thereof. Also provided are such activator compositions additionally comprising a support, e.g., wherein the support comprises a metal-oxide support, and wherein the metal-oxide support comprises silica, alumina, or silica-alumina. Also provided are catalysts comprising an activator composition of this invention and a metallocene or non-metallocene single-site catalyst precursor. Also provided are catalysts comprising an activator composition of this invention, a metallocene or non-metallocene single-site catalyst precursor, and a support.

Activator compositions of this invention can be used in a variety of catalysts, both supported and unsupported.

DETAILED DESCRIPTION OF THE INVENTION

This invention will be described in connection with specific embodiments. It is understood that this invention is not limited to any one of these specific embodiments.

(A) Activator Compositions

Activator compositions of this invention comprise an anion/cation ion pair wherein (a) the anion comprises (i) a metal atom and (ii) an organic ligand having at least two hetero atoms and being chelated to the metal atom through covalent bonding of at least the two hetero atoms with the metal atom, and (b) the cation comprises a Bronsted acid.

(A)(i) Anions

Anions of this invention comprise two key elements: (i) a metal atom and (ii) an organic ligand having at least two hetero atoms and being chelated to the metal atom through covalent bonding of at least two of the hetero atoms with the metal atom. The metal atom typically comprises aluminum (Al), but can comprise any metal in Groups 2-10, Group 13, or the lanthanide or actinide series, as identified in a Periodic Table of the Elements using the new IUPAC format (i.e., current IUPAC format).

The organic ligand has at least two hetero atoms and is chelated to the metal atom through covalent bonds of at least two of the hetero atoms with the metal atom. Optionally, one or more of the hetero atoms of the ligand (not including the hetero atoms that are chelated to the metal atom through covalent bonding) can be bonded to the metal atom through coordinate covalent bonding. Suitable organic ligand precursors are $H_y$(Ch-L), wherein y is 2, 3, or 4, Ch-L is the organic ligand comprising (y+q) hetero atoms, $H_y$ is y hydrogen radicals, each attaching to one of the y hetero atoms on the organic ligand, and q is 0, 1, or 2. One or more of the q hetero atoms can optionally bond to the metal atom through coordinate covalent bonding.

Examples with q=0 are as follows:
When

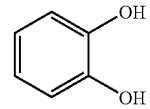

is represented by $H_y$(Ch-L), y=2 and Ch-L=

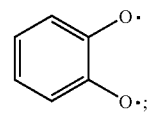

and
when

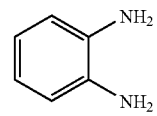

is represented by $H_y$(Ch-L), then y=2 and Ch-L=

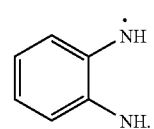

Examples with q=1 are as follows:
When

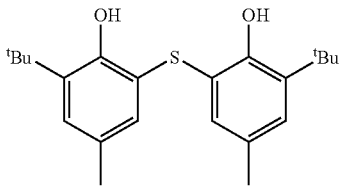

is represented by Hy(CH-L), then y=2 and Ch-L=

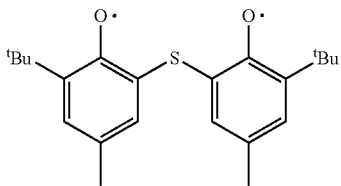

and when

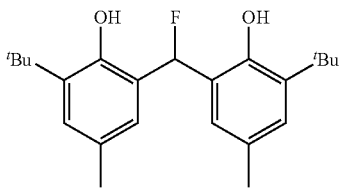

is represented by Hy(CH-L), then y=2 and Ch-L=

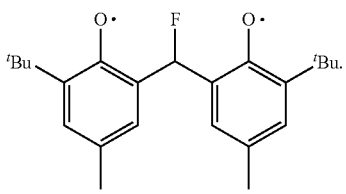

Suitable diol organic ligands include, but are not limited to, the following: Catechol, 3-methylcatechol, 3-fluorocatechol, 3-methoxycatechol, 3,5-di-tert-butylcatechol, 3,5-di-isopropylcatechol, 3,4,5,6-tetrafluorocatechol, 2,2'-biphenol, 1,2-dihydroxynaphthalene, 2,3-dihydroxynaphthalene, 1-phenyl-1,2-ethandiol, 1,2-diphenyl-1,2-ethanediol, 1,1,2-triphenyl-1,2-ethanediol, benzopinacole, hydrobenzoin, 2,3-diphenyl-2,3-butanediol, bis(2-hydroxyphenyl)methane, 2,2'-methylidnebis(4-chlorophenol), 2,2'-ethylidene-bis(4,6-di-tert-butylphenol), 2,2'-methylidene-bis(4-methyl-6-tert-butylphenol), 2,2'-methylidene-bis(4-fluorophenol), hexachlorophene, 1,2-benzenedimethanol, and the like.

Suitable diamine organic ligands include, but are not limited to, the following: 1,2-phenylenediamine, N-methyl-N'-methyl-1,2-phenylenediamine, N-phenyl-N'-phenyl-1,2-phenylenediamine, N-phenyl-N'-methyl-1,2-phenylenediamine, 2,3-diaminotoluene, 4,5-dimethyl-1,2-phenylenediamine, 1,1'-binaphthyl-2,2'-diamine, N-phenyl-N'-phenyl-1,1'-binaphthyl-2,2'-diamine, and the like.

Suitable aminoalcohol organic ligands include, but are not limited to, the following: 3-amino-2-naphthol, 2-amino-1,2-diphenylethanol, N-phenyl-1,1-diphenylglycinol, and the like.

Anions of this invention can be represented as:

$$[M'^{m+}(Ch-L)_n Q_{(m-yn+1)}]^-, \text{ wherein}$$

M is a metal selected from Groups 2-10, Group 13, Lanthanide group, or Actinide group;
m+ is the valence of the metal M';
y=2, 3, or 4;
Ch-L is an organic ligand comprising (y+q) hetero atoms, at least two of which y hetero atoms are (sometimes, each of which is) covalently bonded to the metal M', wherein q is 0, 1, or 2 and when q is 1 or 2 one or more of which q hetero atoms are optionally bonded to the metal M' through coordinate covalent bonding;
n=1, 2, or 3 and yn+1< or =m; and
each Q is selected, independently, from halide radicals, dialkylamido radicals, alkoxide and aryloxide radicals, hydrocarbyl and substituted-hydrocarbyl radicals and organometalloid radicals.

(A)(ii) Cations

Cations of this invention can comprise a proton $[H]^+$ or a neutral Lewis base stabilized proton, and can be represented by the general formula $[HA_x]^+$ wherein H is a proton, A comprises a neutral Lewis base, x is 0, 1 or 2, and when x is 2, the A's are the same or different.

(A)(iii) Anion/Cation Pairs

Broadly, ion pairs of activator compositions of this invention may be represented as follows:

$$[HA_x]^+ [M'^{m+}(Ch-L)_n Q_{(m-2y+1)}]^-, \text{ wherein}$$

H is a proton;
A is a neutral Lewis base;
x=0, 1 or 2, and when x is 2, the A's are the same or different;
M' is a metal selected from Groups 2-10, Group 13, Lanthanide group, or Actinide group;
m+ is the valence of the metal M';
y=2, 3, or 4;
Ch-L is an organic ligand comprising (y+q) hetero atoms, at least two of which y hetero atoms are (sometimes, each of which is) covalently bonded to the metal M', wherein q is 0, 1, or 2 and when q is 1 or 2 one or more of which q hetero atoms are optionally bonded to the metal M' through coordinate covalent bonding;
n=1, 2, or 3 and yn+1< or =m; and
each Q is selected, independently, from halide radicals, dialkylamido radicals, alkoxide and aryloxide radicals, hydrocarbyl and substituted-hydrocarbyl radicals and organometalloid radicals.

Suitable starting materials for anion/cation ion pairs of this invention comprise:

a) a source of metal M', $M'^{m+}Q_m$, where M' is a metal selected from Groups 2-10, Group 13, Lanthanide group, or Actinide group; m is the valence of the metal M'; and each Q independently comprises at least one or more of: halide radical, pseudo-halide radical, dialkylamido radical, alkoxide radical, aryloxide radical, hydrocarbyl radical, substituted-hydrocarbyl radical, and organometalloid radicals; and b) a source of organic ligand Ch-L, $H_y(Ch-L)$, wherein
(i) y=2, 3, or 4;
(ii) Ch-L is an organic ligand comprising (y+q) hetero atoms, at least two of which y hetero atoms are (sometimes, each of which is) covalently bonded to the metal M', wherein q is 0, 1, or 2 and when q is 1 or 2, one or more of which q hetero atoms are optionally bonded to the metal M' through coordinate covalent bonding; and (iii) if $Q_m$ comprises hydrocarbyl radical, substituted-hydrocarbyl radical, dialkylamido radical, organometalloid radical, electron-donating aryloxide radical (for example, 2,6-di-$^t$Bu-4-methylphenoxide radical), including mixtures thereof, when $H_y$(Ch-L) is combined with $M'''^+Q_m$ the following reaction (Reaction (1)) can occur:

$$nH_y(\text{Ch-L}) + M'''^+Q_m = [H]^+[M'''^+(\text{Ch-L})_n Q_{(m-yn+1)}]^- + (yn-1)HQ \quad (1);$$

and if $Q_m$ comprises halide radical, pseudo-halide radical, alkoxide radical, electron-withdrawing aryloxide radical (for example, pentafluorophenoxide radical), including mixtures thereof, M" (where M" comprises a Group 1 metal (alkali metal) cation or ammonium cation) can be combined with $H_y$(Ch-L) to convert $H_y$(Ch-L) to $M''_y$(Ch-L) through the reaction of $H_y$(Ch-L) with, for example, LiBu to form $Li_y$(Ch-L), or M''' (where M''' comprises a Group 2 metal (alkali earth metal)) can be combined with $H_y$(Ch-L) to convert $H_y$(Ch-L) to $M'''_{y/2}$(CH-L) through the reaction of $H_y$(Ch-L) with, for example, $MgEt_2$ to form $Mg_{y/2}$(CH-L) and $M'''^+Q_m$ can be converted to $[H]^+[M'''^+Q_{m+1}]^-$ through the reaction of HQ with $M'''^+Q_m$; such that Reaction (2) or (3) can occur:

$$nM''_y(\text{Ch-L}) + [H]^+[M'''^+Q_{m+1}]^- = [H]^+[M'''^+(\text{Ch-L})_n Q_{(m-yn+1)}]^- + ynM''Q \quad (2);$$

$$nM'''_{y/2}(\text{Ch-L}) + [H]^+[M'''^+Q_{m+1}]^- = [H]^+[M'''^+(\text{Ch-L})_n Q_{(m-2y+1)}]^- + (y/2)nM'''Q_2 \quad (3)$$

to result in formation of $[H]^+[M'''^+(\text{Ch-L})_n Q_{(m-yn+1)}]^-$; and, optionally, c) a neutral Lewis base A, which is capable of interacting with $[H]^+$ generated in Reactions (1), (2), or (3) to form a compound $[HA_x]^+[M'''^+(\text{Ch-L})_n Q_{(m-2y+1)}]^-$. Suitable Lewis bases include, without limitation, Lewis bases based on N, O, P or S, including amines and ethers. Neutral Lewis base A can comprise a) one or more linear ethers, one or more cyclic ethers or mixtures of linear and cyclic ethers or b) one or more secondary amines, one or more tertiary amines, or mixtures of secondary and tertiary amines. For example, without limiting this invention, the Lewis base can comprise one or more of the following: a) ethers $P'_2O$, where P' is a hydrocarbyl group having 1 to about 20 carbon atoms, such as diethylether $Et_2O$, and the like, or $P'_2$ is an organic diradical having about 4 to about 12 carbon atoms to form cyclic ethers, such as tetrahydrofuran (THF), and the like and b) amines $NR^1_2$ or $NR^1_3$, wherein $R^1$ in each occurrence is selected independently from hydrocarbyl group having up to about 20 carbon atoms, or hydrogen, such as $NMe_3$, $NEt_3$, $NMe_2Ph$, $NMe_2(CH_2Ph)$, $NEt_2Ph$, $NEt_2(CH_2Ph)$, $NMe(C_jH_{2j+1})(C_kH_{2k+1})$, $NMe_2(C_jH_{2j+1})$, $NEt(C_jH_{2j+1})(C_kH_{2k+1})$, and $NEt_2(C_jH_{2j+1})$, where j and k are each independently an integer from 3 to 20.

Activator compositions of this invention can comprise a metal atom, an organic ligand, and a Bronsted acid, wherein (a) the organic ligand comprises at least y hetero atoms and is chelated to the metal atom through covalent bonding of at least two of the y hetero atoms with the metal atom; and (b) the Bronsted acid comprises $[HA_x]^+$, wherein H is a proton, A comprises a neutral Lewis base, and x is 0, 1, or 2, and when x is 2, the A's are the same or different.

This invention provides methods for preparing activator composition comprising combining triethylaluminum and 2,2'-ethylidenebis(4,6-di-t-butylphenol).

The invention provides methods for preparing activator composition comprising combining one equivalent of triethylaluminum and two equivalents of 2,2'-ethylidenebis(4,6-di-t-butylphenol).

This invention provides methods for preparing activator composition comprising combining triethylaluminum, 2,2'-ethylidenebis(4,6-di-t-butylphenol), and either N,N-dimethylaniline or N,N-dimethylbenzylamine.

(B) Catalyst Precursors

Metallocene and non-metallocene single-site catalyst precursors (B), suitable for activation by activator compositions of this invention, can comprise one or more alkylated transition metal component having olefin polymerization potential. The alkyl ligand of the precursor functions as a leaving group upon reaction of the precursor with the proton of the Bronsted acid of the activator composition. For example, without limiting this invention, hydrocarbyl is a suitable alkylated transition metal ligand. Provided that suitable alkylation agent is provided in situ, halogen, alkoxy, aryloxy, and amide transition metal components are all suitable.

Catalyst precursors (B) can comprise catalyst precursor $ML_aX_{n-a}$.

M represents any transition metal catalyst compound in which the transition metal thereof is in Group 3 to 10, or in the lanthanide or actinide series, of the Periodic Table of Elements using the new IUPAC format, for example, the Periodic Table appearing on page 27 of the Feb. 4, 1985 issue of *Chemical & Engineering News*. Suitable catalyst compounds can also be described as d- and f-block metal compounds. See, for example, the Periodic Table appearing on page 225 of Moeller, et al., *Chemistry*, Second Edition, Academic Press, copyright 1984. Metal constituent of M may comprise Fe, Co, Ni, and Pd, and may comprise metals of Groups 4-6 (Ti, Zr, Hf, V, Nb, Ta, Cr, Mo, and W).

Thus catalyst precursors (B) used in this invention can be one or more of any Ziegler-Natta catalyst compound, any metallocene, any single-site non-metallocene, any compound of constrained geometry, any late transition metal complex, and any other transition metal compound or complex reported in the literature or otherwise generally known in the art to be an effective catalyst compound when suitably activated, including mixtures of at least two different types of such transition metal compounds or complexes, such as for example a mixture of a metallocene and a Ziegler-Natta olefin polymerization catalyst compound.

L represents group having ligand suitable for either Ziegler-Natta type catalyst precursor, or metallocene type catalyst precursor, or non-metallocene single-site catalyst precursor. At least one L may be group having cyclopentadienyl skeleton, or may be non-cyclopentdienyl; and a plurality of L may be the same or different and may be crosslinked to each other; X represents halogen, alkoxy, aryloxy, amide or hydrocarbyl group having 1 to about 20 carbon atoms; "a" represents a numeral satisfying the expression $0 < a \leq n$; and n represents valence of transition metal atom M.

In L in catalyst precursors (B), group having cyclopentadienyl skeleton can comprise, for example, cyclopentadienyl group, substituted cyclopentadienyl group or polycyclic group having cyclopentadienyl skeleton. Example substituted cyclopentadienyl groups include hydrocarbon group having 1 to about 20 carbon atoms, halogenated hydrocarbon group having 1 to about 20 carbon atoms, silyl group having 1 to about 20 carbon atoms and the like. Silyl group according to this invention can include $SiMe_3$ and the like. Examples of polycyclic group having cyclopentadienyl skeleton include indenyl group, fluorenyl group and the like. Examples of hetero atom of the group having at least one hetero atom include nitrogen atom, oxygen atom, phosphorous atom, sulfur atom and the like.

Example non-metallocene d-block or f-block metal compounds that can be used in this invention include, but are not limited to, transition metal compounds suitable for olefin polymerization such as Ziegler-Natta type catalysts. Typically, transition metal of Ziegler-Natta catalysts comprises at least two hydrocarbyl ligands. Examples of Ziegler-Natta catalyst systems are disclosed in U.S. Patent Application Number 2004/0102312, and are described herein as follows. Representative traditional Ziegler-Natta transition metal compounds include, but are not limited to, tetrabenzyl zirconium, tetrakis(trimethylsilylmethyl)zirconium, oxotris(trimethylsilylmethyl)vanadium, tetrabenzyl hafnium, tetrabenzyl titanium, bis(hexamethyl disilazido)dimethyl titanium, tris (trimethylsilylmethyl)niobium dichloride, tris(trimethylsilylmethyl)tantalum dichloride, and combinations thereof. Other Ziegler-Natta type systems that can be used in this invention include, but are not limited to, transition metal halides, oxyhalides or alkoxyhalides in the presence of an alkylating agent such as a dialkylaluminum alkoxide or trialkyl aluminum compound. Examples of this Ziegler-Natta type system include, but are not limited to, titanium and vanadium halides, oxyhalides or alkoxyhalides, such as titanium tetrachloride ($TiCl_4$), vanadium tetrachloride ($VCl_4$) and vanadium oxytrichloride ($VOCl_3$), and titanium and vanadium alkoxides, wherein the alkoxide moiety has a branched or unbranched alkyl group from 1 to 20 carbon atoms, or from 1 to 6 carbon atoms. Any chloride-containing catalyst precursor is suitable once alkylated, including via in-situ alkylation, by methods well-known to those skilled in the art.

In still another aspect, useful d-block or f-block metal compounds that can be used in this invention include, but are not limited to, the Group 15-containing compounds, such as those disclosed in U.S. Patent Application Number 2004/0102312, and defined above. Examples of Group 15-containing compounds include, but are not limited to, Group 4 iminophenol complexes, Group 4 bis(amido) complexes, and Group 4 pyridyl-amide complexes that are active towards olefin polymerization to any extent. In one aspect, the Group 15-containing catalyst component can be described by the following formula:

$\beta_b(\alpha)_a\gamma_g MX_n$; wherein:

$\beta$ and $\gamma$ are groups that each comprise at least one Group 14 to Group 16 atom; and $\beta$ (when present) and $\gamma$ are groups bonded to M through from 1 to 4 Group 14 to Group 16 atoms, wherein at least two atoms are Group 15-containing atoms; more particularly: $\beta$ and $\gamma$ are groups selected from Group 14 and Group 15-containing (and their non-valent equivalents when not linked by a group $\alpha$): alkyls, aryls, alkylaryls, and heterocyclic hydrocarbons, and chemically bonded combinations thereof in one aspect; and selected from Group 14 and Group 15-containing: $C_1$ to $C_{10}$ alkyls, $C_5$ to $C_{12}$ aryls, $C_6$ to $C_{18}$ alkylaryls, and $C_4$ to $C_{12}$ heterocyclic hydrocarbons, and chemically bonded combinations thereof in a further aspect; and selected from $C_1$ to $C_{10}$ alkylamines, $C_1$ to $C_{10}$ alkoxys, $C_6$ to $C_{20}$ alkylarylamines, $C_6$ to $C_{18}$ alkylaryloxys, and $C_4$ to $C_{12}$ nitrogen containing heterocyclic hydrocarbons, and $C_4$ to $C_{12}$ alkyl substituted nitrogen containing heterocyclic hydrocarbons and chemically bonded combinations thereof in still another aspect; and selected from anilinyls, pyridyls, quinolyls, pyrrolyls, pyrimidyls, purinyls, imidazyls, indolyls, $C_1$ to $C_6$ alkyl substituted groups selected from anilinyls, pyridyls, quinolyls, pyrrolyls, pyrimidyls, purinyls, imidazyls, indolyls: $C_1$ to $C_6$ alkylamine substituted groups selected from anilinyls, pyridyls, quinolyls, pyrrolyls, pyrimidyls, purinyls, imidazyls, indolyls, amine substituted anilinyls, pyridyls, quinolyls, pyrrolyls, pyrimidyls, purinyls, imidazyls, and indolyls; hydroxy substituted groups selected from anilinyls, pyridyls, quinolyls, pyrrolyls, pyrimidyls, purinyls, imidazyls, and indolyls; methyl-substituted phenylamines, and chemically bonded combinations thereof in yet a further aspect: $\alpha$ can be a linking (or "bridging") moiety that, when present, forms a chemical bond to each of $\beta$ and $\gamma$, or to two $\gamma$ moieties, thus forming a "$\gamma\alpha\gamma$" or "$\gamma\alpha\beta$" ligand bound to M; $\alpha$ can also include a Group 14 to Group 16 atom which can be bonded to M through the Group 14 to Group 16 atom in one aspect; and more particularly, $\alpha$ can be a divalent bridging group selected from alkylenes, arylenes, alkenylenes, heterocyclic arylenes, alkylarylenes, heteroatom containing alkylenes, heteroatom containing alkenylenes and heterocyclic hydrocarbonylenes in another aspect; and selected from $C_1$ to $C_{10}$ alkylenes, $C_2$ to $C_{10}$ alkenylenes, $C_6$ to $C_{12}$ arylenes, $C_1$ to $C_{10}$ divalent ethers, $C_6$ to $C_{12}$ O- or N-containing arylenes, $C_2$ to $C_{10}$ alkyleneamines, $C_6$ to $C_{12}$ aryleneamines, and substituted derivatives thereof in yet a further aspect;

a is typically 0 or 1;

b is typically an integer from 0 to 2;

g is an integer from 1 to 2; wherein in one aspect, a is 1, b is 0, and g is 2;

M is selected from Group 3 to Group 12 atoms in one aspect; and selected from Group 3 to Group 10 atoms in a further aspect; and selected from Group 3 to Group 6 atoms in yet another aspect; and selected from Ni, Cr, Ti, Zr and Hf in still a further aspect; and selected from Zr and Hf in yet one other aspect; each X represents halogen, alkoxy, aryloxy, amide or hydrocarbyl group having 1 to about 20 carbon atoms; and n is an integer from 0 to 4 in one aspect; and an integer from 1 to 3 in another aspect; and an integer from 2 to 3 in still another aspect.

As used in this description, "chemically bonded combinations thereof" means that adjacent groups, ($\beta$ and $\gamma$ groups) can form a chemical bond between them; in one aspect, the $\beta$ and $\gamma$ groups are chemically bonded through one or more $\alpha$ groups there between.

As used herein, the terms "alkyleneamines", "aryleneamines", describe alkylamines and arylamines (respectively) that are deficient by two hydrogens, thus capable of forming chemical bonds with two adjacent y groups, or adjacent $\beta$ and $\gamma$ groups. Thus, examples of an alkyleneamine include, but are not limited to, $—CH_2CH_2N(CH_3)CH_2CH_2—$ and $—CH_2CH_2N(H)CH_2CH_2—$. Examples of a heterocyclic hydrocarbylene or aryleneamine include, but are not limited to, $—C_5H_3N—$ (divalent pyridine). An "alkylene-arylamine" includes a group such as, for example, $—CH_2CH_2(C_5H_3N)CH_2CH_2—$.

Examples of compounds having the genera formula $\beta_b(\alpha)_a\gamma_g MX_n$ include, but are not limited to, the following compounds:

1.

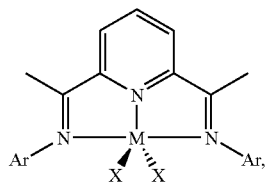

including compounds such as those disclosed in WO 99/02472, wherein examples of Ar include 2-$MeC_6H_4$, 2,4, 6-$Me_3C_6H_2$, 2-i-$PrC_6H_4$, and the like; and examples of M include Fe or Ni; and examples of X include Cl, Br, or a $C_1$ to $C_{12}$ hydrocarbyl;

2.

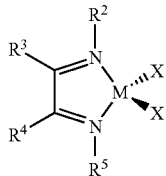

including compounds such as those disclosed in U.S. Pat. No. 5,880,241, wherein examples of $R^2$ and $R^5$ (as used therein) include 2,6-i-$Pr_2C_6H_3$, 2,6-$Me_2C_6H_3$, and 2,4,6-$Me_3C_6H_2$; examples of $R^3$ and $R^4$ (as used therein) include methyl, ethyl, propyl, butyl, and benzyl; examples of M include Pd and Ni; and examples of X include Cl, Br, and a $C_1$ to $C_{12}$ hydrocarbyl such as Me;

3.

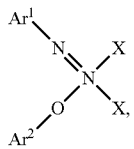

including compounds such as those disclosed in Nomura et al., *Macromolecules*, 2005, in press (Abstract published by the American Chemical Society, *Macromolecules*, ASAP Article 10.1021/ma050829s; S0024-9297(05)00629-7; Web Release Date Jun. 15, 2005), wherein examples of $Ar^1$ include 2,6-$Me_2C_6H_3$ and 2,6-i-$Pr_2C_6H_3$; examples of $Ar^2$ include 2,6-$Me_2C_6H_3$, 2,4,6-$Me_3C_6H_2$, 2,6-i-$Pr_2C_6H_3$, and 2,6-$Ph_2C_6H_3$; examples of M include V; and examples of X include Cl, Br, and a $C_1$ to $C_{12}$ hydrocarbyl;

4.

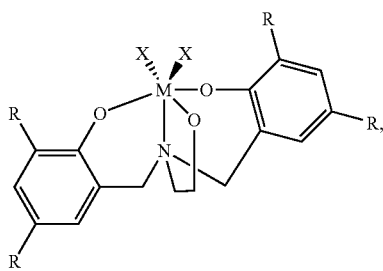

including compounds such as those disclosed in Waymouth et al., *Macromolecules*, 2005, 38, 2552-2558, wherein examples of M include Zr or Hf; examples of X include a $C_1$ to $C_{12}$ hydrocarbyl such as $CH_2C_6H_5$; examples of R (as used therein) include Me, Ph, or t-Bu; and examples of D include $NMe_2$, OMe, and the like; and 5. any combination of the above compounds, In each of these compounds, if X is a halide or alkoxide, these metal compounds typically are used in conjunction with an alkylating agent such as a trialkyl aluminum or alkoxyaluminum dialkyl reagent to convert these compounds to the corresponding dialkyl species.

Example substituted cyclopentadienyl groups include methylcyclopentadienyl group, ethylcyclopentadienyl group, n-propylcyclopentadienyl group, n-butylcyclopentadienyl group, isopropylcyclopentadienyl group, isobutylcyclopentadienyl group, sec-butylcyclopentadienyl group, tertbutylcyclopentadienyl group, 1,2-dimethylcyclopentadienyl group, 1,3-dimethylcyclopentadienyl group, 1,2,3-trimethylcyclopentadienyl group, 1,2,4-trimethylcyclopentadienyl group, tetramethylcyclopentadienyl group, pentamethylcyclopentadienyl group and the like.

Example polycyclic groups having cyclopentadienyl group include indenyl group, 4,5,6,7-tetrahydroindenyl group, fluorenyl group and the like.

Example groups having at least one hetero atom include methylamino group, tert-butylamino group, benzylamino group, methoxy group, tert-butoxy group, phenoxy group, pyrrolyl group, thiomethoxy group and the like.

One or more groups having cyclopentadienyl skeleton, or one or more group having cyclopentadienyl skeleton and one or more group having at least one hetero atom, may be crosslinked with (i) alkylene group such as ethylene, propylene and the like; (ii) substituted alkylene group such as isopropylidene, diphenylmethylene and the like; or (iii) silylene group or substituted silylene group such as dimethylsilylene group, diphenylsilylene group, methysilylsilylene group and the like.

Examples of transition metal component $ML_aX_{n-a}$, wherein M comprises zirconium, include bis(cyclopentadienyl)zirconiumdichloride, bis(methylcyclopentadienyl)zirconiumdichloride, bis(pentamethylcyclopentadienyl)zirconium dichloride bis(indenyl)zirconiumdichloride, bis(4,5,6,7-tetrahydroindenyl)zirconiumdichloride, bis(fluorenyl)zirconiumdichloride, ethylenebis(indenyl)zirconiumdichloride, dimethylsilylene (cyclopentadienylfluorenyl)zirconiumdichloride, diphenylsilylenebis(indenyl)zirconiumdichloride, cyclopentadienyldimethylaminozirconiumdichloride, cyclopentadienylphenoxyzirconium dichloride, dimethyl(tert-butylamino)(tetramethylcyclopentadienyl) silanezirconiumdichloride, isopropylidene(cyclopentadienyl)(3-tert-butyl-5-methyl-2-phenoxy)zirconiumdichloride, dimethylsilylene(tetramethylcyclopentadienyl)(3-tert-butyl-5-methyl-2-phenoxy)zirconiumdichloride and the like.

Additional exemplary transition metal component $ML_aX_{n-a}$ include components wherein zirconium is replaced with titanium or hafnium in the above zirconium components.

Alkylated catalyst precursors useful in this invention are: rac-dimethylsilylbis(2-methyl-4-phenyl-indenyl)zirconium dimethyl; rac-dimethylsilylbis(2-methyl-1-indenyl)zirconium dimethyl; rac-dimethylsilylbis(2-methyl-4,5-benzoindenyl) zirconium dimethyl; ethylenebis(tetrahydroindenyl) zirconium dimethyl, and ethylenebis(indenyl)zirconium dimethyl. Alkylated catalyst precursor can be generated in-situ through reaction of alkylation agent with the halogenated version of the catalyst precursor. For example, bis(cyclopentadienyl)zirconium dichloride can be treated with triisobutylaluminum (TIBA) and then combined with activator composition (A) of this invention.

Additional non-limiting and representative metallocene compounds that can be used in the present invention include mono-cyclopentadienyl compounds such as pentamethylcyclopentadienyl titanium trimethyl, pentamethylcyclopentadienyl titanium tribenzyl, dimethylsilyltetramethyl-cyclopentadienyl-tert-butylamido titanium dimethyl, dimethylsilyltetramethylcyclopentadienyl-tert-butylamido zirconium dimethyl, dimethylsilyltetramethylcyclopentadienyl-dodecylamido hafnium dihydride, dimethylsilyltetramethylcyclopentadienyl-dodecylamido hafnium dimethyl, unbridged biscyclopentadienyl compounds such as bis (1,3-butylmethylcyclopentadienyl)zirconium dimethyl, bis (1,3-butylmethylcyclopentadienyl)zirconium dibenzyl, pentamethylcyclopentadienyl-cyclopentadienyl zirconium dimethyl, (tetramethylcyclopentadienyl)(n-propylcyclopetadienyl)zirconium dimethyl; bridged bis-cyclopentadienyl compounds such as dimethylsilylbis(tetrahydroindenyl)zirconium dimethyl and silacyclobutyl(tetramethylcyclopentadienyl)(n-propyl-cyclopentadienyl) zirconium dimethyl; bridged bisindenyl compounds such as dimethylsilylbis(indenyl) zirconium dimethyl, dimethylsilylbis(indenyl)zirconium dibenzyl, dimethylsilylbis(indenyl) hafnium dimethyl, dimethylsilylbis(2-methylbenzindenryl)zirconium dimethyl, dimethylsilylbis(2-methylbenzindenyl)zirconium dibenzyl; and fluorenyl ligand-containing compounds, for example, diphenylmethyl(fluorenyl)(cyclopentadienyl)zirconium dimethyl; and the additional mono- and bis-cyclopentadienyl compounds such as those listed and described in U.S. Pat. Nos. 5,017,714 and 5,324,800, and in EP-A-0 591 756.

(C) Catalyst Carrier/Support

Carrier/support (C) comprises an inorganic carrier or an organic carrier. A plurality of carriers can be used as a mixture, and support (C) may contain water, e.g., as absorbed water or in hydrate form. Support (C) can comprise a metal-oxide support. A metal-oxide support (C) can comprise silica, alumina, or silica-alumina. Support (C) can be porous and have a micro pore volume of not less than 0.1 ml/g of silica, or not less than 0.3 ml/g. Support (C) can have a micro pore volume of about 1.6 ml/g of silica. The average particle diameter of support (C) can be from about 5 micrometers to about 1000 micrometers, or from about 10 micrometers to about 500 micrometers.

A silica useful in this invention is porous and has a surface area in the range of from about 10 $m^2/g$ silica to about 700 $m^2/g$ silica, a total pore volume in the range of from about 0.1 cc/g silica to about 4.0 cc/g silica, and an average particle diameter in the range of from about 10 micrometers to about 500 micrometers. The silica can have a surface area in the range of from about 50 $m^2/g$ to about 500 $m^2/g$, a pore volume in the range of from about 0.5 cc/g to about 3.5 cc/g, and an average particle diameter in the range of from about 15 micrometers to about 150 micrometers. The silica can have a surface area in the range of from about 200 $m^2/g$ to about 350 $m^2/g$, a pore volume in the range of from about 1.0 cc/g to about 2.0 cc/g, and an average particle diameter in the range of from about 10 micrometers to about 110 micrometers.

Average pore diameter of a porous silicon dioxide carrier (C) can be in the range of from about 10 angstroms to about 1000 angstroms, or can be from about 50 angstroms to about 500 angstroms, or from about 175 angstroms to about 350 angstroms. The content of hydroxyl groups can be from about 0.04 mmol OH/g silica to about 3.0 mmol OH/g silica, with or without the presence of free hydroxyl groups, as determined by the following Grignard reaction. Most of these active OH groups react readily with benzylmagnesium chloride Grignard to produce to produce toluene, and this reaction can be used to quantify the concentration of active OH groups on a particular silica. The content of hydroxyl groups can be from about 0.10 mmol OH/g silica to about 2.0 mmol OH/g silica, or from about 0.4 mmol OH/g silica to about 1.5 mmol OH/g silica.

Example inorganic carriers that may be useful in this invention include inorganic oxides, magnesium compounds, clay minerals and the like. Example inorganic oxides useful in this invention include, without limitation, $SiO_2$, $Al_2O_3$, MgO, $ZrO_2$, $TiO_2$, $B_2O_3$, CaO, ZnO, BaO, $ThO_2$ and double oxides thereof, e.g. $SiO_2$—$Al_2O_3$, $SiO_2$—MgO, $SiO_2O$-$iO_2$, $SiO_2$—$TiO_2$—MgO. Example magnesium compounds useful in this invention include $MgCl_2$, MgCl(OEt) and the like. Example clay minerals useful in this invention include kaolin, bentonite, kibushi clay, geyloam clay, allophane, hisingerite, pyrophylite, talc, micas, montmorillonites, vermiculite, chlorites, palygorskite, kaolinite, nacrite, dickite, halloysite and the like.

Example organic carriers that may be useful in this invention include acrylic polymer, styrene polymer, ethylene polymer, propylene polymer and the like. Example acrylic polymers that may be useful in this invention include polymers of acrylic monomers such as acrylonitrile, methyl acrylate, methyl methacrylate, methacrylonitrile and the like, and copolymers of the monomers and crosslinking polymerizable compounds having at least two unsaturated bonds. Example styrene polymers that may be useful in this invention include polymers of styrene monomers such as styrene, vinyltoluene, ethylvinylbenzene and the like, and copolymers of the monomers and crosslinking polymerizable compounds having at least two unsaturated bonds. Example crosslinking polymerizable compound having at least two unsaturated bonds include divinylbenzene, trivinylbenzene, divinyltoluene, divinylketone, diallyl phthalate, diallyl maleate, N,N'-methylenebisacrylamide, ethylene glycol dimethacrylate, polyethylene glycol dimethacrylate and the like.

In this invention, organic carrier can have at least one polar functional group. Examples of suitable polar functional groups include primary amino group, secondary amino group, imino group, amide group, imide group, hydrazide group, amidino group, hydroxy group, hydroperoxy-group, carboxyl group, formyl group, methyloxycarbonyl group, carbamoyl group, sulfo group, sulfino group, sulfeno group, thiol group, thiocarboxyl group, thioformyl group, pyrrolyl group, imidazolyl group, piperidyl group, indazolyl group and carbazolyl group. When the organic carrier originally has at least one polar functional group, the organic carrier can be used as it is. One or more kinds of polar functional groups can also be introduced by subjecting the organic carrier as a matrix to a suitable chemical treatment. The chemical treatment may be any method capable of introducing one or more polar functional groups into the organic carrier. For example, it may be a reaction between acrylic polymer and polyalkylenepolyamine such as ethylenediamine, propanediamine, diethylenetriamine, tetraethylenepentamine, dipropylenetriamine or the like. As the specific method of such a reaction, for example, there is a method of treating an acrylic polymer (e.g. polyacrylonitrile) in a slurry state in a mixed solution of ethylenediamine and water at 100° C. or more, for example from 120° C. to 150° C. In this invention, the amount of polar functional group per unit gram in the organic carrier having a polar functional group can be from 0.01 to 50 mmol/g, or from 0.1 to 20 mmol/g.

(D) Catalyst

Catalysts according to this invention comprise/are derived from activator composition (A) and catalyst precursor (B), and optionally, support (C).

Polymerization Using Activator Composition of this Invention

In the present invention, any olefin or diolefin having 2 to 20 carbon atoms can be used as a monomer for polymerization. Specific examples thereof include ethylene, propylene, butene-1, pentene-1, hexene-1, heptene-1, octane-t, nonene-1, decene-1, hexadecene-1, eicocene-1,4-methylpentene-1,5-methyl-2-pentene-1, vinylcyclohexane, styrene, dicyclopentadiene, norbornene, 5-ethylidene-2-norbornene and the like, but are not limited thereto. In the present invention, copolymerization can be conducted using two or more monomers, simultaneously. Specific examples of the monomers constituting the copolymer include ethylene/an α olefin such as ethylene/propylene, ethylene/butene-1, ethylene/hexene-1, ethylene/propylene/butene-1, ethylene/propylene/5-ethylidene-2-norbornene and the like, propylene/butene-1, and the like, but are not limited thereto.

The polymerization method is not limited, and both liquid phase polymerization method and gas phase polymerization method can be used. Examples of solvent used for liquid phase polymerization include aliphatic hydrocarbons such as butane, pentane, heptane, octane and the like; aromatic hydrocarbons such as benzene, toluene and the like; and hydrocarbon halides such as methylene chloride and the like. It is also possible to use at least a portion of the olefin to be polymerized as a solvent. The polymerization can be conducted in a batch-wise, semibatch-wise or continuous manner, and polymerization may be conducted in two or more stages which differ in reaction conditions. The polymerization temperature can be from about −50° C. to about 200° C., or from 0° C. to about 100° C. The polymerization pressure can be from atmospheric pressure to about 100 kg/cm², or from atmospheric pressure to about 50 kg/cm². Appropriate polymerization time can be determined by means known to those skilled in the art according to the desired olefin polymer and reaction apparatus, and is typically within the range from about 1 minute to about 20 hours. In the present invention, a chain transfer agent such as hydrogen may be added to adjust the molecular weight of olefin polymer to be obtained in polymerization.

In this invention, organoaluminum compound can be added during polymerization to remove impurities, such as water. Organoaluminum compound useful herein can comprise a variety of organoaluminum compounds, including at least one currently known organoaluminum compound, for example, organoaluminum compound $R^3_c AlY_{3-c}$ (wherein $R^3$ represents a hydrocarbon group having 1 to about 20 carbon atoms; Y represents hydrogen atom and/or halogen atoms; and "c" represents an integer of 0 to 3). Specific examples of $R^3$ include methyl group, ethyl group, n-propyl group, n-butyl group, isobutyl group, n-hexyl group, n-octyl group, and the like. Specific examples of the halogen atom for Y include fluorine atom, chlorine atom, bromine atom and iodine atom. Specific examples of the organoaluminum compound $R^3_c AlY_{3-c}$ include trialkylaluminums such as trimethylaluminum, triethylaluminum, tri-n-propylaluminum, triisobutylaluminum, tri-n-hexylaluminum, trioctylaluminum and the like; dialkylaluminum chloride such as dimethylaluminum chloride, diethylaluminum chloride, di-n-propylaluminum chloride, diisobutylaluminum chloride, di-n-hexylaluminum chloride and the like: alkylaluminum dichlorides such as methylaluminumdichloride, ethylaluminum dichloride, n-propylaluminum dichloride, isobutylaluminum dichloride, n-hexylaluminum dichloride and the like; and dialkylaluminum hydrides such as dimethylaluminum hydride, diethylaluminum hydride, di-n-propylaluminum hydride, diisobutylaluminum hydride, di-n-hexylaluminum hydride and the like.

EXAMPLES

In the following examples, structures consistent with obtained NMR data are shown. However, this invention is not limited by the structures shown in the following examples.

Example 1

Preparation of Activator Composition EX1AC of this Invention —[Al(L1)₂]⁻[HNPhMe₂]⁺

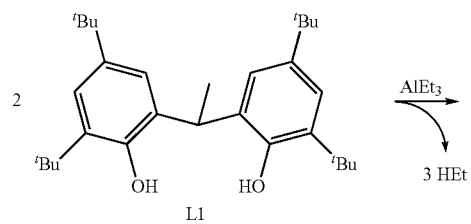

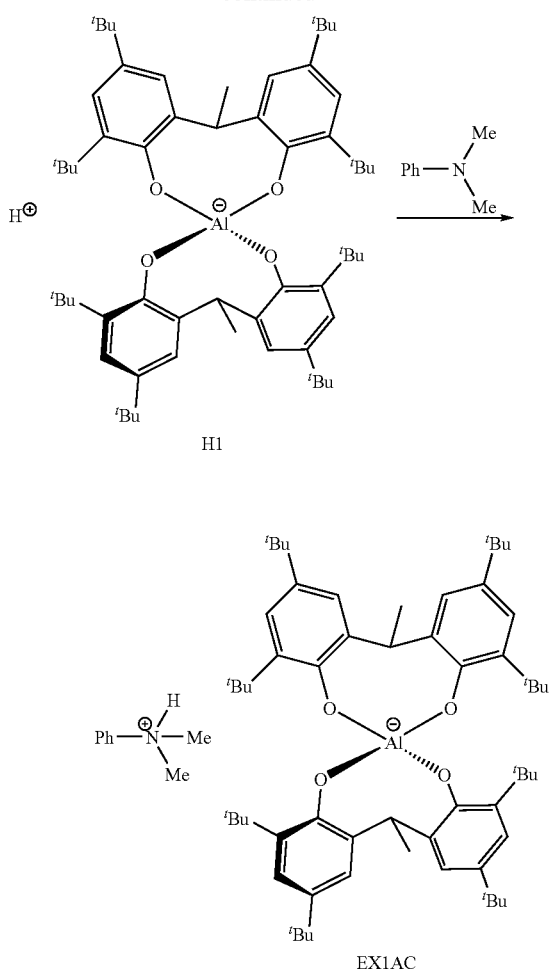

1.14 g (10 mmol) triethylaluminum (TEA) and 2.5 g dry isohexane were charged to a 20 mL vial. 8.77 g (20 mmol) 2,2'-ethylidene-bis(4,6-di-tert-butylphenol) (L1) and 23 g isohexane were charged to an 8 oz wide-mouth bottle with a stirbar. While stirring, the TEA solution was slowly added to the L1 slurry over 15 minutes. The slurry eventually became a deep red transparent solution (H1). 1.21 g (10 mmol) PhNMe₂ was slowly added to the deep red solution. The mixture was allowed to stir at ambient for 2 hours. White precipitate formed. The white solid was isolated by filtration, washed three times with 10 mL isohexane, and dried under vacuum. 6.4 g white solid (63%) was obtained (EX1AC). EX1AC analysis results: 1H NMR (THF-d8, 21° C.): δ1.2-1.5 (4 s, 72H, -$^t$Bu); δ1.6 (d, 3H, HC—CH₃); δ2.6 (s, 6H, —N Me₂); δ5.4 (q, 1H, H—CCH₃); δ6.9-7.5 (m, 13H, aromatic H); δ8.2 (s (br), 1H, N—H). ICP: Al, calculated: 2.64 wt %, found: 2.65 wt %. Grignard titration for active proton (ClMgCH₂Ph): N—H calculated: 100%; found: 99.7%. Homogeneous polyethylene polymerization test according to procedure in Example 9: 1.1×10⁵ g/g Zr/hr (2.15 micromol rac-ethylenebis(indenyl)zirconocene dimethyl (M1), 40° C., 50 PSi, 1,200 mL cyclohexane, 2 mL 25% (BHT)₂AlMe in isohexane as scavenger, EX1AC:Zr=1.1:1, 10 minutes).

Example 2

Preparation of Activator Composition EX2AC of this Invention —[Al(L1)₂]⁻[HNCH₂PhMe₂]⁺

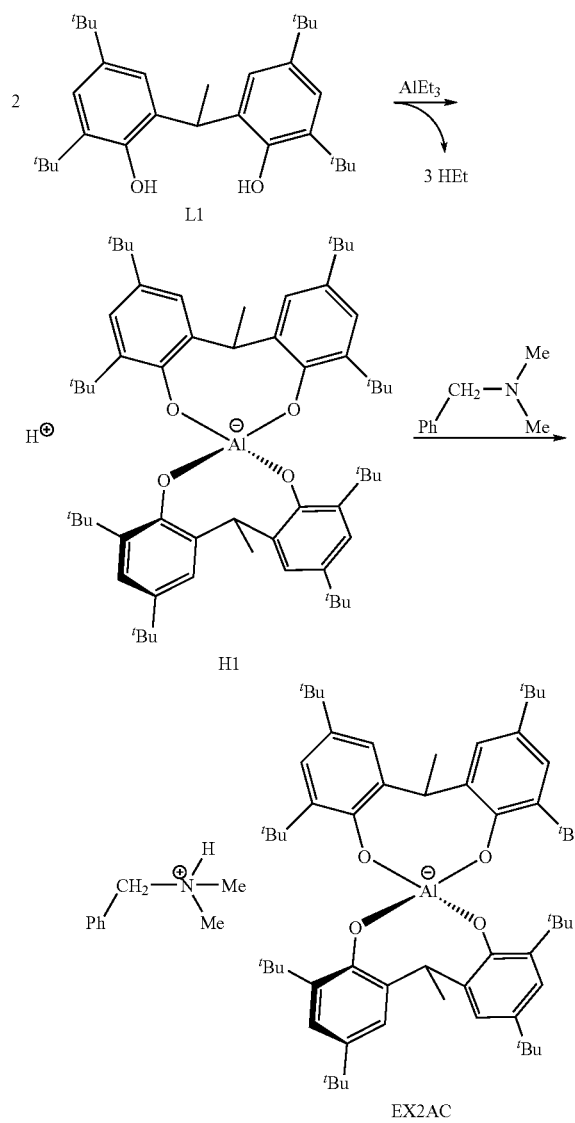

EX2AC 0.114 g (1 mmol) triethylaluminum (TEA) and 4 g dry isohexane were charged to a 4 mL vial. 0.877 g (2 mmol) 2,2'-ethylidene-bis(4,6-di-tert-butylphenol) (L1) and 2 g isohexane were charged to a 4 oz wide-mouth bottle with a stirbar. While stirring, the TEA solution was then added dropwise added to the L1 slurry. The slurry was stirred in a 60° C. oil-bath for 15 min. White precipitate formed (H1). 5 g toluene was added. The slurry became an orange solution. After cooling to room temperature, white precipitate was observed again. 0.135 g (1 mmol) PhCH₂NMe₂ was added to the slurry. The slurry changed to colorless. The slurry was allowed to stir overnight. More solid formed. The mixture was filtered, washed two times with 10 mL isohexane, and dried under vacuum overnight. Yield: 0.38 g (EX2AC). EX2AC analysis results: 1H NMR (THF-d8, 21°C.): δ1.2-1.5 (4 s, 72H, -ᵗBu); δ1.6 (d, 3H, HC—CH₃); δ2.6 (s, 6H, —NMe₂); δ5.4 (q, 1H, H—CCH₃); δ4.0 (s, 2H, CH₂); δ6.9-7.5 (m, 13H, aromatic H); δ8.2 (s (br), 1H, N—H). The material was able to activate rac-ethylenebis(indenyl)zirconocene dimethyl (M1) for 1-hexene polymerization, according to the following procedure: 10 mg (26.5 micro mol) M1 and 1 g toluene were charged to a 4 mL vial. Then 28.8 mg (27.8 micro mol) EX2AC in 0.5 g toluene was added to the M1 solution, followed by vigorous shaking for 5 min to form a red brown solution. Then 0.9 g dry 1-hexene was added at once through a pipette. The red brown solution began to boil and resulted in a dark gel.

Example 3

Preparation of an Activator Composition EX3AC of this Invention—[Al(L2)₂]⁻[HPhNMe₂]⁺

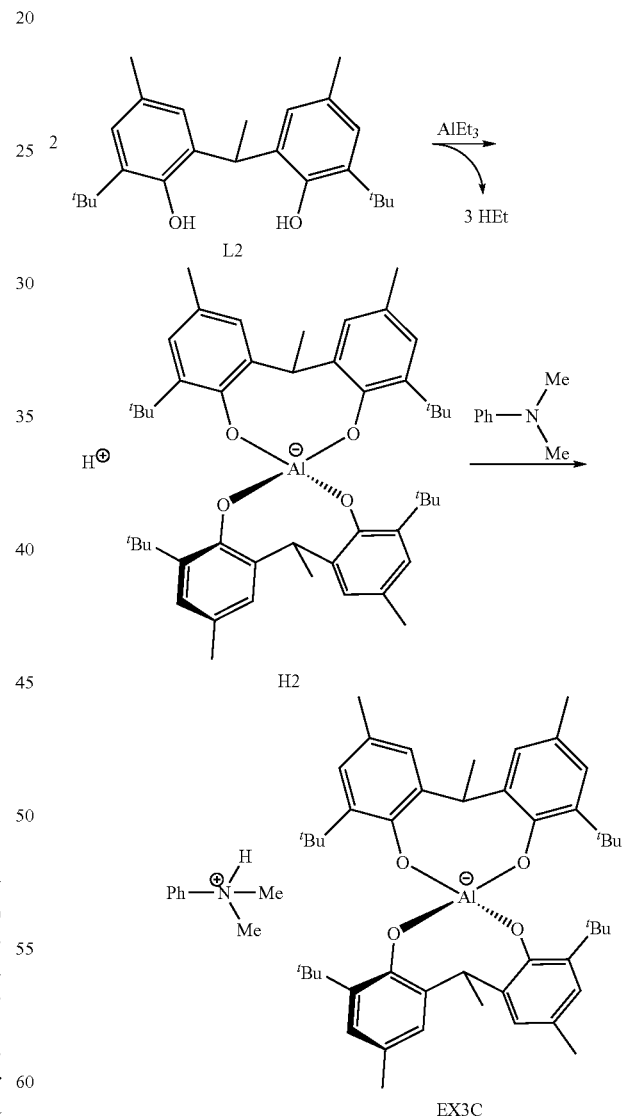

EX3C 1.14 g (10 mmol) triethylaluminum (TEA) and 2.5 g dry toluene were charged to a 20 mL vial. 6.81 g (20 mmol) methylidene-bis(4-methyl-6-tert-butylphenol) (L2) and 25 g toluene were charged to an 8 oz wide-mouth bottle with a stirbar. While stirring, the TEA solution was then slowly added to the L2 slurry. After ⅘ of the TEA solution was added, white solid formation was observed. The slurry was allowed to stir in a 75° C. oil-bath for 1 hour and eventually became a deep brown transparent solution (H2). The reaction bottle was removed from the oil-bath and allowed to cool to ambient temperature and stir overnight. 1.21 g (10 mmol) PhNMe$_2$ in 3 g toluene was slowly added to the deep brown solution. The mixture was allowed to stir at 75° C. for 1 hr. White precipitate formed. A large amount of white solids formed and prohibited the stirbar from stirring. 30 g isohexane was then added to allow for more precipitation. The white solid was isolated by filtration, washed three times with 10 mL isohexane, and dried under vacuum for 1.5 hr. 5.8 g white solid (72%) was obtained, 2$^{nd}$ and 3$^{rd}$ crops were obtained by adding more isohexane for the precipitation of the product, giving a total yield 7.2 g (88%) (EX3AC). Pre-contact of this activator (EX3AC) with a structurally more open metallocene such as rac-ethylenebis(indenyl)zirconocene dimethyl (M1) yielded no stable active species. Polymerization was observed only when the catalyst precursor was co-charged with 1-hexene before contact with the activator (EX3AC). The following polymerization procedure was used: 10 mg (26.5 micro mol) M1 and 1 g toluene were charged to a 4 mL vial. Then 0.9 g dry 1-hexene was added at once through a pipette. Then 23.0 mg (27.8 micro mol) EX3AC in 0.5 g toluene was added to the M1 solution, followed by vigorous shaking for 5 min to form a red brown solution. The red brown solution began to boil, resulting in a dark gel.

Example 4 (Comparative Example)

Attempted Preparation of [Al(BHT)$_4$]$^-$ [HPhNMe$_2$]$^+$ (Non-Chelating Structure)

Attempt to synthesize EX4BHT did not succeed even at high temperatures (e.g., 100° C.). Instead of the desired EX4BHT structure with four BHT units attached to Al, a compound containing only two BHT units attached to Al (BAB) was obtained. The material did not show any activity for metallocene dialkyl activation and did not polymerize 1-hexene. The following polymerization procedure was used: 10 mg (26.5 micro mol) M1 and 1 g toluene were charged to a 4 mL vial. Then 0.9 g dry 1-hexene was added at once through a pipette. Then 0.5 g of solution containing DBAB, amine and BHT was added to the M1 solution, followed by vigorous shaking for 5 min. No color change was observed. The solution did not polymerize 1-hexene.

Example 5

Preparation of Activator Composition EX5AC of this Invention—[$^t$BuAl(BHT)(L1)]$^-$[H]$^+$

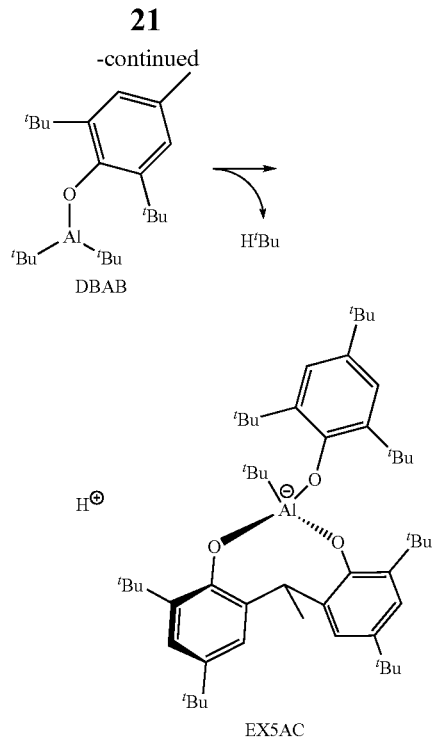

1.0 g (1.0 mmol) DBAB solution (36% or 1 mmol/g, made from TIBA with equal mole of 2,6-di-t-Bu-4-methylphenol (BHT)) was charged into a 20 mL vial. 0.439 g (1.0 mmol) L1 was added to the DBAB solution. Precipitation was immediately observed. The mixture was tested for both rac-dimethylsilylbis(2-methyl-4-phenyl-indenyl)zirconiumdimethyl (M2) and rac-ethylenebis(indenyl)zirconocene dimethyl (M1) activation and both were activated for 1-hexene polymerization, according to the following procedure: 10 mg (26.5 micro mot) M1 and 1 g toluene were charged to a 4 mL vial. Then 0.9 g dry 1-hexene was added at once through a pipette. Then 0.5 g solution containing EX5AC was added to the M1 solution, followed by vigorous shaking for 5 min to form a red brown solution. The red brown solution began to boil, resulting in a dark gel.

Example 6

Preparation 1 of Silica Supported Catalysts Using Activator EX1AC of this Invention 1.34 g IBAO (isobutylaluminoxane, containing 5-7 wt % Al, made from the reaction of triisobutylaluminum with 70-90 mol % water based on Al) coated silica (made from 600° C. calcined Grace 952 silica treated with IBAO at 90 to 100° C. for 3 hr) was charged in a 20 mL vial. 34 mg M2, 1 g toluene, and 62.6 mg EX1AC obtained from Example 1 were added to another 20 mL vial to form a slurry. The slurry was mixed with the IBAO coated silica solid and the mixture was stirred with a glass rod for 5 min. The color changed from yellow to deep red. The wet red solid was then placed under vacuum to dry for 2 hr. Yield: 1.43 g (pink red). Polypropylene polymerization test according to procedure in Example 11: 10,300 g/g cat/hr with TIBA as scavenger and slight reactor fouling was observed; 9,000 g/g cat/hr without scavenger and no reactor fouling was observed.

Example 7

Preparation 2 of Silica Supported Catalysts Using Activator EX1AC of this Invention 2.0 g EAO (Ethylaluminoxane, containing 4-5 wt % Al, made from the reaction of triethylaluminum with 70-80 mol % water based on Al) coated silica (made from 600° C. calcined Grace 952 silica treated with EAO at 90-100° C. for 3 hr, containing 7% Al) was charged in a 20 mL vial. 69 mg M2, 3 g toluene, and 125 mg EX1AC obtained from Example 1 were added to another 20 mL vial to form the slurry. The slurry was mixed with the EAO coated silica solid and the mixture was shaken for 60 min. The color changed from yellow to deep red. The wet red solid was then placed under vacuum to dry for 3 hr. Yield: 2.3 g (brown orange). Polypropylene polymerization test according to procedure in Example 11: 9,000 g/g cat/hr without scavenger and no reactor fouling was observed.

Example 8

Preparation 3 of Silica Supported Catalysts Using Activator EX1AC of this Invention 2.8 g EAO (containing 4-5 wt % Al, made from the reaction of triethylaluminum with 70-80 mol % water based on Al) coated silica (made from 600° C. calcined Grace 952 silica treated with EAO at 90-100° C. for 3 hr, containing 7% Al) and 135 mg EX1AC obtained from Example 1 were charged into a 20 mL vial and mixed well on a shaker for 30 min. 52 mg M1, 0.33 g 1-hexene and 3 g toluene were added to another 20 mL vial. The M1/1-hexene solution was then added slowly to the mixture of EAO coated silica solid and the mixture was shaken on a shaker for 30 min. The color changed from yellow to pink. The wet red solid was then placed under vacuum to dry for 2 hr. Yield: 3.1 g (pink). Polyethylene polymerization test according to procedure in Example 10: 300 g/g cat/hr without scavenger and slight reactor fouling was observed.

Example 9

Homogeneous PE—Standard Polymerization Procedure

Preparation of M1 Solution in Drybox:
M1 solution was prepared in a drybox by weighing 7.0-13.0 mg of solid M1 compound into a 20 mL vial. Dry toluene was added to make a solution with a concentration of 2.15 micromol/g. The vial was capped and shaken to form a solution.

Reactor Pre-Set: The reactor temperature was set to desired temperature. $N_2$ was flushed from the reactor three times with ethylene, each time pressuring to 50 psi, then venting to 0 psi. Added to the reactor was: total 1200 mL isohexane with 2 mL 25% $(BHT)_2AlMe$ solution through the 600 mL solvent bomb. The reactor temperature was equilibrated with the agitator at a low speed.

Preparation of Active Catalyst Solution: A 5 mL dried syringe was tared without the needle on the balance in the dry box. A desired amount of activator solution was weighed into the syringe based on Al:Zr=1.1:1. 1.00 g M1 solution was added into the syringe with the activator sample. A 12 inch 18 gauge needle was attached to the syringe, the needle was capped with a crimp-top vial, and the time that the pre-contact solution was completed was noted.

Addition of Active Catalyst Solution to Reactor: Active catalyst solution was removed from the drybox. The agitator was stopped; the pressure was vented down and the temperature of the solvent was noted. The injector port valve was opened, the crimp-top vial was removed from the needle tip and the entire needle shaft was inserted into the injector port. The active catalyst solution was injected into the reactor, the needle was removed, the injector port was closed, the agitator was started to about 850 rpm, and then the ethylene valve was quickly opened to begin pressuring the reactor with ethylene.

Reaction Conditions: Run time was 10 or 30 minutes; pressure and agitator speed were controlled at 50 psi and 800-825 rpm, respectively; starting temperature was 40° C., but increased to 60° C. in 10 minutes, at which time the reaction was stopped.

Reaction Quenching: Polymerization reactions were ended by closing the ethylene valve and stopping the agitator.

Polymer Treatment: Polymer was dried to constant weight by filtering the slurry in methanol through a vacuum flask with a filter funnel and drying in vacuum oven.

Example 10

Supported PE—Standard Polymerization Procedure

A 4 L reactor was dried by heating at 100° C. for 15 minutes minimum under low pressure nitrogen flow. After cooling to ambient, the reactor was pressurized with isobutane and vented three times to remove nitrogen. Isobutane (1000 ml) was charged into the reactor while adding 40 ml of dried 1-hexene with or without a scavenger. The reactor agitator was set at 800 rpm. After flushing the charging line with 700 ml of isobutane, the reactor was charged with ethylene up to 320 psi for supported M1 while at the same time bringing the temperature of the reactor up to 80° C. Then, 50-100 mg of solid catalyst was slurried in 2 ml of hexane in the glovebox and then injected into the reactor followed by 100 ml of isobutane. The reaction pressure was maintained at 320 psi and the polymerization was carried out for 1 hour at 80° C. The reaction was stopped by venting off the ethylene and isobutane. The polymer was isolated, dried, and weighed.

Example 11

Supported PP—Standard Polymerization Procedure

The general procedures for propylene polymerization were as follows. A 4-L autoclave reactor that had been dried under a nitrogen flow at a temperature of >100° C., was charged with 2 L of propylene and 25 mmol of hydrogen. The reactor temperature was raised to 70° C., while the sample was stirred at 700 rpm. In cases in which a scavenger was used, a 2 mL-sample of a 10 wt % TIBA solution in hexane was injected into the reactor. Then 40 mg of catalyst was injected into the reactor, using 300 mL as a flush. The reaction mixture was stirred at 70° C. for one hour. At the end of the test, the polymerization was stopped by venting the reactor and opening it to the atmosphere, and the resulting polypropylene was collected.

ADVANTAGES OF THIS INVENTION

Activator compositions of this invention are capable of activating catalysts with commercially reasonable rates of deactivation without requiring use of relatively expensive perfluoro groups.

While the present invention has been described in terms of one or more preferred embodiments, it is to be understood that other modifications may be made without departing from the scope of the invention, which is set forth in the claims below.

I claim:

1. A catalyst composition comprising a metallocene or non-metallocene single-site catalyst precursor; and an activator composition comprising an anion/cation ion pair, wherein
    (a) the anion comprises (i) a metal atom and (ii) an organic ligand having at least two hetero atoms and being chelated to the metal atom through covalent bonding of at least the two hetero atoms with the metal atom, and
    (b) the cation comprises a Bronsted acid.

2. The catalyst composition of claim 1 wherein the metal atom comprises a metal selected from Groups 2-10, Group 13, or the lanthanide or actinide series of the Periodic Table of the Elements.

3. The catalyst composition of claim 2 wherein the metal atom comprises Al.

4. The catalyst composition of claim 1 wherein the Bronsted acid comprises $[HA_x]^+$, wherein H is a proton, A comprises a neutral Lewis base, x is 0, 1 or 2, and when x is 2, the A's are the same or different.

5. The catalyst composition of claim 1, wherein the activator composition is derived from at least:
    (a) $M'^{m+}Q_m$, where M' is a metal selected from Groups 2-10, Group 13, Lanthanide group, or Actinide group; m is the valence of the metal M'; and each Q independently comprises at least one or more of: halide radical, dialkylamido radical, alkoxide radical, aryloxide radical, hydrocarbyl radical, substituted-hydrocarbyl radical, and organometalloid radicals; and
    (b) $H_y$(Ch-L), wherein (i) y is 2, 3, or 4; (ii) Ch-L is an organic ligand comprising y hetero atoms, at least two of the y hetero atoms being capable of forming a covalent bond with the metal M', and (iii) $H_y$ is y hydrogen radicals, each hydrogen radical being bonded to one of the y hetero atoms.

6. The catalyst composition of claim 5, wherein the activator composition is additionally derived from:
    (a) a neutral Lewis base.

7. The catalyst composition of claim 6, wherein the activator composition further comprises a support.

8. The catalyst composition of claim 5, wherein the activator composition further comprises a support.

9. The catalyst composition of claim 1, wherein the activator composition is derived from at least:
    (a) $M'^{m+}Q_m$, where M' is a metal selected from Groups 2-10, Group 13, Lanthanide group, or Actinide group; m is the valence of the metal M'; and each Q independently comprises at least one or more of: halide radical, dialkylamido radical, alkoxide radical, aryloxide radical, hydrocarbyl radical, substituted-hydrocarbyl radical, and organometalloid radicals; and
    (b) $H_y$(Ch-L), wherein (i) y is 2, 3, or 4; (ii) Ch-L is an organic ligand comprising (y+q) hetero atoms, at least two of the y hetero atoms being capable of forming a covalent bond with the metal M', q is 0, 1 or 2, and, optionally, one or more of the q hetero atoms is capable of forming a coordinate covalent bond with the metal M', and (iii) $H_y$ is y hydrogen radicals, each hydrogen radical being bonded to one of the y hetero atoms.

10. A catalyst composition comprising a metallocene or non-metallocene single-site catalyst precursor; and an activator composition comprising a metal atom, an organic ligand, and a Bronsted acid, wherein:

(a) the organic ligand comprises at least 2 hetero atoms and is chelated to the metal atom through covalent bonding of at least two of the hetero atoms with the metal atom; and
(b) the Bronsted acid comprises $[HA_x]^+$, wherein H is a proton, A comprises a neutral Lewis base, and x is 0, 1 or 2, and when x is 2, the A's are the same or different.

11. The catalyst composition of claim 10, wherein the neutral Lewis base comprises: a) one or more linear ethers, one or more cyclic ethers or mixtures thereof or b) one or more secondary amines, one or more tertiary amines, or mixtures thereof.

12. The catalyst composition of claim 10, additionally comprising a support.

13. The catalyst composition of claim 12, wherein the support comprises a metal-oxide support.

14. The catalyst composition of claim 13, wherein the metal-oxide support comprises silica, alumina, or silica-alumina.

15. The catalyst composition of claim 1, further comprising a support.

* * * * *